(12) United States Patent
Nishimura et al.

(10) Patent No.: US 8,951,199 B2
(45) Date of Patent: Feb. 10, 2015

(54) ULTRASONIC DIAGNOSTIC APPARATUS THAT PERFORMS GAIN CONTROL BASED ON OFFSET PATTERNS OF PIXEL BRIGHTNESS

(75) Inventors: Yuushi Nishimura, Kanagawa (JP); Manabu Migita, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 711 days.

(21) Appl. No.: 12/559,518

(22) Filed: Sep. 15, 2009

(65) Prior Publication Data

US 2010/0069755 A1 Mar. 18, 2010

(30) Foreign Application Priority Data

Sep. 18, 2008 (JP) ................................. 2008-239228

(51) Int. Cl.
*A61B 8/00* (2006.01)
*A61B 8/14* (2006.01)
*G01S 7/52* (2006.01)

(52) U.S. Cl.
CPC ............... *A61B 8/14* (2013.01); *G01S 7/52033* (2013.01); *G01S 7/52034* (2013.01); *G01S 7/5205* (2013.01); *G01S 7/52073* (2013.01); *A61B 8/58* (2013.01)
USPC ....................................................... 600/443

(58) Field of Classification Search
USPC .................................................. 600/437, 443
See application file for complete search history.

(56) References Cited

U.S. PATENT DOCUMENTS

| 4,945,915 | A | * | 8/1990 | Nagasaki | 600/443 |
| 5,579,768 | A | * | 12/1996 | Klesenski | 600/442 |
| 5,671,744 | A | * | 9/1997 | Abe et al. | 600/443 |
| 6,102,859 | A | | 8/2000 | Mo | |
| 7,645,236 | B2 | * | 1/2010 | Simopoulos et al. | 600/437 |
| 2007/0016024 | A1 | * | 1/2007 | Simopoulos et al. | 600/437 |
| 2007/0236492 | A1 | * | 10/2007 | Ahn et al. | 600/437 |
| 2007/0265530 | A1 | * | 11/2007 | Hashimoto et al. | 600/443 |

FOREIGN PATENT DOCUMENTS

| JP | 05-253226 | 10/1993 |
| JP | 06-114060 | 4/1994 |
| JP | 2000-197637 | 7/2000 |
| JP | 2005-152422 | 6/2005 |

* cited by examiner

*Primary Examiner* — Unsu Jung
*Assistant Examiner* — Phong K Huynh
(74) *Attorney, Agent, or Firm* — Lucas & Mercanti, LLP

(57) ABSTRACT

An ultrasonic diagnostic apparatus including a transmitter section for driving a probe so that a subject is scanned with an ultrasonic beam over a predetermined period of time; a receiver section for receiving, using the probe, an echo resulting from the ultrasonic beam being reflected by the subject, and producing a receive signal for each passage of the predetermined period of time; an image constructing section for producing a tomographic image frame composed of brightness information based on an intensity of the receive signal for each passage of the predetermined period of time, and adjusting brightness of the produced tomographic image frame with a set gain; a gain control section for producing the set gain; and a display section for displaying the tomographic image frame whose brightness has been adjusted.

13 Claims, 7 Drawing Sheets

ULTRASONIC DIAGNOSTIC APPARATUS THAT PERFORMS GAIN CONTROL BASED ON OFFSET PATTERNS OF PIXEL BRIGHTNESS

BACKGROUND OF THE INVENTION

1. Field of the Invention

The present invention relates to an ultrasonic diagnostic apparatus, and more particularly to an ultrasonic diagnostic apparatus capable of displaying tomographic images.

2. Description of the Related Art

An ultrasonic diagnostic apparatus enables the user to observe the inside of a subject by irradiating the subject with an ultrasonic wave, and analyzing information contained in the echo signal thereof. A commonly-used conventional ultrasonic diagnostic apparatus images the anatomy of a subject, in the form of a tomographic image, by converting the intensity of an echo signal to the brightness of the corresponding pixel. This enables the user to know the internal anatomy of the subject.

Generally, an ultrasonic wave attenuates while propagating through a subject. This generally decreases the intensity of the reflection wave obtained from inside the subject. Where a two-dimensional tomographic image is obtained by scanning a subject with an ultrasonic wave, the intensity of the reflection wave obtained through the scan may vary depending on, for example, the degree of contact between the subject and the probe. Such variation in the reflection intensity lowers the detection sensitivity in detecting a receive signal based on the reflection wave.

In order to correct such variations in the detection sensitivity, Japanese Laid-Open Patent Publication Nos. 2000-197637 and 2005-152422 disclose techniques for adjusting correction values in DGC (Depth Gain Control) for correcting the sensitivity in the depth direction, and LGC (Lateral Gain Control) for correcting the sensitivity in the scan (lateral) direction.

Specifically, Japanese Laid-Open Patent Publication No. 2000-197637 discloses a technique including: dividing an image frame into a regular grid of kernels; comparing the mean pixel intensity with the mean noise level predicted using a noise model for each kernel; selecting kernels in which the mean pixel intensity is greater than the mean noise level by a predetermined quantity and calculating the mean value of the mean pixel intensities of these kernels to thereby calculate the row/column mean of pixel intensity; and using the difference between the mean value and the reference value as the correction value. The publication also discloses performing a gain adjustment which will suppress the noise for each row/column in which the number of un-selected kernels is less than a critical threshold.

Japanese Laid-Open Patent Publication No. 2005-152422 discloses a technique of obtaining the mean signal intensity for each depth of the image, and obtaining a correction value as the difference between the reference value and the normalized mean value, which is obtained by normalizing the mean signal intensities. The publication also discloses weighting the correction value by setting the weight to 1 when the variance value of the signal intensity for each depth is greater than the reference value and setting the weight to less than 1 when the variance value is smaller than the reference value.

In the methods disclosed in Japanese Laid-Open Patent Publication Nos. 2000-197637 and 2005-152422, the pixel intensity and the variance value are used as index values for noise determination. With these methods, however, the pixel intensity lowers due to the attenuation of the transmitted wave deep inside the body, and it is difficult to accurately identify, for example, a non-noise image with a low variance value such as an image of the inside of a liver.

The methods disclosed in Japanese Laid-Open Patent Publication Nos. 2000-197637 and 2005-152422 are effective in equalizing the gain level and suppressing noise, but are not suitable for emphasizing an anatomical tissue component in the image, e.g., by increasing the gain level for the parts of interest, such as vessel walls in carotid diagnosis, relative to the gain level of other regions, thereby making the image easier to view.

Moreover, since the methods disclosed in Japanese Laid-Open Patent Publication Nos. 2000-197637 and 2005-152422 use DGC and LGC for correcting the gain of the image, the unit of correction is either by degrees of depth or by scanning lines. Therefore, in a case where the image includes an anatomical tissue component that extends two-dimensionally, such as the inside of the ventricle of the heart or in the vessels of the abdominal region, the gain correction varies in the scan direction or in the depth direction so that an area that should appear with even brightness may appear with uneven brightness.

SUMMARY OF THE INVENTION

An objective of the present invention is to solve such problems in the prior art, and to provide an ultrasonic diagnostic apparatus, with which it is possible to obtain a tomographic image with an appropriate gain level without the operator performing a complicated operation.

An ultrasonic diagnostic apparatus of the present invention includes: a transmitter section for driving a probe so that a subject is scanned with an ultrasonic beam over a predetermined period of time; a receiver section for receiving, using the probe, an echo resulting from the ultrasonic beam being reflected by the subject, and producing a receive signal for each passage of the predetermined period of time; an image constructing section for producing a tomographic image frame composed of brightness information based on an intensity of the receive signal for each passage of the predetermined period of time, and adjusting brightness of the produced tomographic image frame with a set gain; a gain control section for producing the set gain; and a display section for displaying the tomographic image frame whose brightness has been adjusted, wherein the gain control section includes: an offset pattern producing section for producing at least one offset pattern based on brightness information for different pixels of the tomographic image frame, the offset pattern including brightness offset values for the different pixels; and a gain determination section for determining the set gain based on at least one gain, selected from among a total gain, a depth-direction gain, a scan-direction gain and a frame gain, based on the offset pattern, wherein the total gain is composed of a single offset value used for the entire tomographic image frame, the depth-direction gain includes offset values used in a depth direction of the tomographic image frame, the scan-direction gain includes offset values used in a scan direction of the tomographic image frame, and the frame gain includes offset values used for different pixels of the tomographic image frame.

In a preferred embodiment, the gain control section produces the set gain based on an instruction from an operator. Thus, the operator can obtain, when desired, a tomographic image with an optimal gain level without performing a complicated operation.

In a preferred embodiment, the ultrasonic diagnostic apparatus further includes a counter for counting the number of the tomographic image frames produced, wherein the gain control section produces the set gain based on the number of the tomographic image frames produced. Thus, the operator can obtain a tomographic image with an optimal gain level without performing any gain-adjustment operation.

In a preferred embodiment, the offset pattern producing section includes: an equalization offset pattern producing section for producing an equalization offset pattern for equalizing a brightness level of the tomographic image frame; and an emphasis/suppression offset pattern producing section for producing an emphasis/suppression offset pattern for emphasizing a tissue while suppressing a noise component in the tomographic image frame, wherein the offset pattern is at least one of the equalization offset pattern and the emphasis/suppression offset pattern. Thus, it is possible to suppress noise while equalizing the gain level across the image, thereby making it easier to see anatomical tissues.

In a preferred embodiment, the equalization offset pattern producing section: divides the tomographic image frame into a plurality of sub-areas; calculates a mean brightness of each sub-area; calculates a brightness difference between the mean brightness of the sub-area and a reference brightness; determines an adjustment value by which the brightness difference is multiplied; determines a product obtained by multiplying the brightness difference by the adjustment value to be an offset value for the sub-area; and calculates the equalization offset pattern including offset values for all pixels of the tomographic image frame based on the offset values for the sub-areas. Thus, it is possible to equalize the gain level while maintaining the contrast of the entire image.

In a preferred embodiment, the reference brightness is a mean brightness for the entire tomographic image frame. Thus, it is possible to obtain an image such that the gain level of the entire tomographic image frame after the brightness adjustment is not substantially different from that before the brightness adjustment.

In a preferred embodiment, the adjustment value is determined based on a brightness value histogram for the sub-area and a brightness value histogram for the entire image frame. Thus, the sub-areas can be classified into low-brightness areas, medium-brightness areas and high-brightness areas, and it is possible to equalize the gain level predominantly in medium-brightness areas.

In a preferred embodiment, the emphasis/suppression offset pattern producing section: divides the tomographic image frame into sub-areas; calculates a feature quantity of each sub-area; normalizes the feature quantity; converts the normalized feature quantity to an offset value; and calculates the emphasis/suppression offset pattern including offset values for all pixels of the tomographic image frame based on the offset values for the sub-areas. Thus, it is possible to suppress the noise level of the image, and to increase the gain level for anatomical tissues.

In a preferred embodiment, the feature quantity is a function of a mean brightness value and a standard deviation of brightness of the sub-area. Thus, it is possible to accurately identify noise components and anatomical tissue components in the image.

In a preferred embodiment, the single offset value of the total gain is a mean value among all pixels of the offset pattern. Thus, it is possible to determine an optimal total gain.

In a preferred embodiment, the gain determination section calculates a mean value among offset values for pixels of the same depth in the offset pattern, and calculates the depth-direction gain by smoothing the mean value in the depth direction. Thus, it is possible to determine an optimal depth-direction gain.

In a preferred embodiment, the gain determination section calculates a mean value among offset values for pixels along the same scan line in the offset pattern, and calculates the scan-direction gain by smoothing the mean value in the scan direction. Thus, it is possible to determine an optimal scan-direction gain.

In a preferred embodiment, the gain control section determines a frequency with which the set gain is produced based on a frame rate at which the tomographic image frame is produced. Thus, it is possible to always maintain an optimal frequency with which an offset pattern is calculated even if the frame rate is changed.

In a preferred embodiment, the gain control section produces a plurality of offset patterns, and sets a frequency of production of each offset pattern based on the number of tomographic image frames produced. Thus, it is possible to more finely adjust the trade-off between the capacity of the gain determination section and the optimal precision.

With the ultrasonic diagnostic apparatus of the present invention, the gain control section two-dimensionally performs a data operation on the data of the tomographic image obtained by transmitting and then receiving an ultrasonic wave, thereby automatically producing a set gain with which the brightness can be adjusted so as to obtain an image that is easier to view. Therefore, it is possible to obtain a tomographic image with such brightness that the image is easy to view without the operator performing a complicated operation.

Other features, elements, processes, steps, characteristics and advantages of the present invention will become more apparent from the following detailed description of preferred embodiments of the present invention with reference to the attached drawings.

DETAILED DESCRIPTION OF PREFERRED EMBODIMENTS

First Embodiment

Figure 1A:
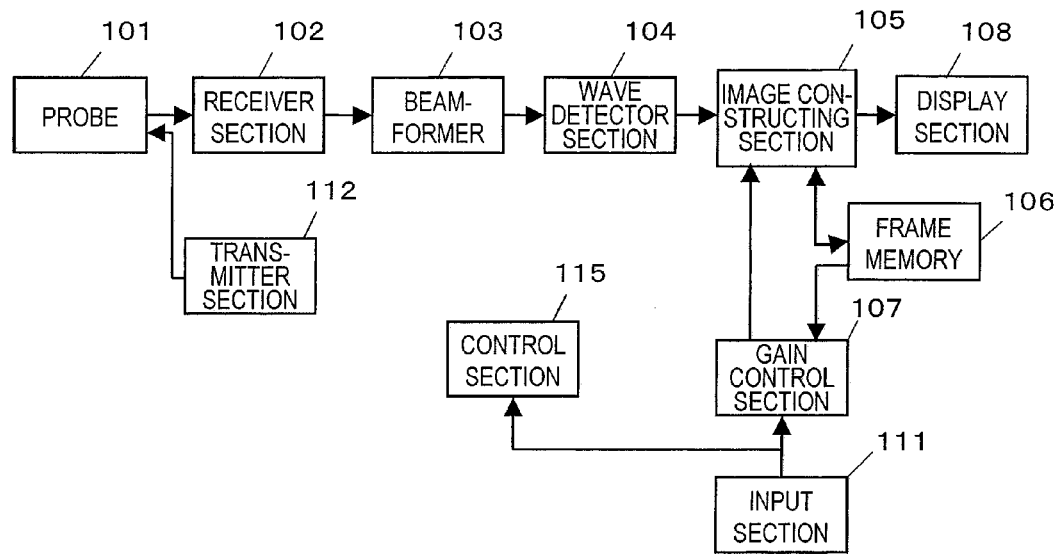
FIG. 1A is a block diagram showing an ultrasonic diagnostic apparatus according to a first embodiment of the present invention.

FIG. 1A is a block diagram showing an ultrasonic diagnostic apparatus according to an embodiment of the present invention. As shown in FIG. 1A, the ultrasonic diagnostic apparatus of the present embodiment includes a transmitter section 112, a receiver section 102, a beamformer 103, a wave detector section 104, an image constructing section 105, a frame memory 106, a gain control section 107 and a display section 108. The ultrasonic diagnostic apparatus also includes a control section 115 for controlling the various sections. An input section 111 to be a user interface, such as a keyboard, a trackball, a switch or a button, is connected to the control section 115, and the control section 115 controls the various sections of the ultrasonic diagnostic apparatus in response to the operator inputting an instruction to the control section 115 via the input section 111. The control section 115 may be a microcomputer, or the like. The beamformer 103, the wave detector section 104, the image constructing section 105, the frame memory 106 and the gain control section 107 have functions to be described in detail below, which may be implemented by software. In that case, the microcomputer of the control section 115 may execute the software, or the ultrasonic diagnostic apparatus may include another microcomputer, or the like, for executing the software.

A probe 101 is connected to the ultrasonic diagnostic apparatus. The probe 101 may be a general-purpose probe, and the ultrasonic diagnostic apparatus of the present embodiment may include the probe 101. It is preferred that the probe 101 has a steering function or is a two-dimensional or three-dimensional array probe so that a two-dimensional tomographic image can be obtained.

Based on the control by the control section 115, the transmitter section 112 produces a driving signal, and outputs the driving signal to the probe 101. The probe 101 includes a plurality of piezoelectric vibrators, and the piezoelectric vibrators vibrate in response to the application of the driving signal to thereby produce an ultrasonic beam. The produced ultrasonic beam is transmitted toward the subject. The probe 101 is driven so that the subject is scanned with the ultrasonic beam for each passage of a predetermined period of time.

The ultrasonic beam reflected by the subject returns to the probe 101 in the form of an echo. The piezoelectric vibrators of the probe 101 successively convert received echoes to electric signals.

The receiver section 102 includes an amplifier and an A/D converter, and successively amplifies the electric signal from the probe 101 to thereby produce a receive signal. The produced receive signal is converted by the A/D converter to a digital signal. Thus, a receive signal is obtained for each passage of the predetermined period of time over which the subject is scanned with the ultrasonic wave.

The beamformer 103 performs a delayed synthesis for combining together receive signals from the piezoelectric vibrators. Thus, it is possible to obtain a receive signal by an echo corresponding to each acoustic line of the ultrasonic beam transmitted so as to scan the subject. The wave detector section 104 performs an envelope detection of the receive signal, and produces intensity information of the receive signal.

The image constructing section 105 receives and filters the intensity information of the receive signal, and then produces the brightness information of each of the pixels forming a tomographic image frame based on the intensity information of the receive signal. The produced brightness information of the tomographic image frame is output to the frame memory 106, and stored in the frame memory 106. These operations are performed in real time. That is, these operations are performed for each passage of the predetermined period of time over which the subject is scanned with the ultrasonic wave.

As will be described below in detail, the image constructing section 105 receives the set gain determined by the gain control section 107, and adjusts the brightness of the tomographic image frame based on the set gain. Moreover, the image constructing section 105 scan-converts data of the tomographic image frame based on the adjusted brightness, and outputs the converted data to the display section 108. The display section 108 displays the data of the tomographic image frame.

Figure 1B:
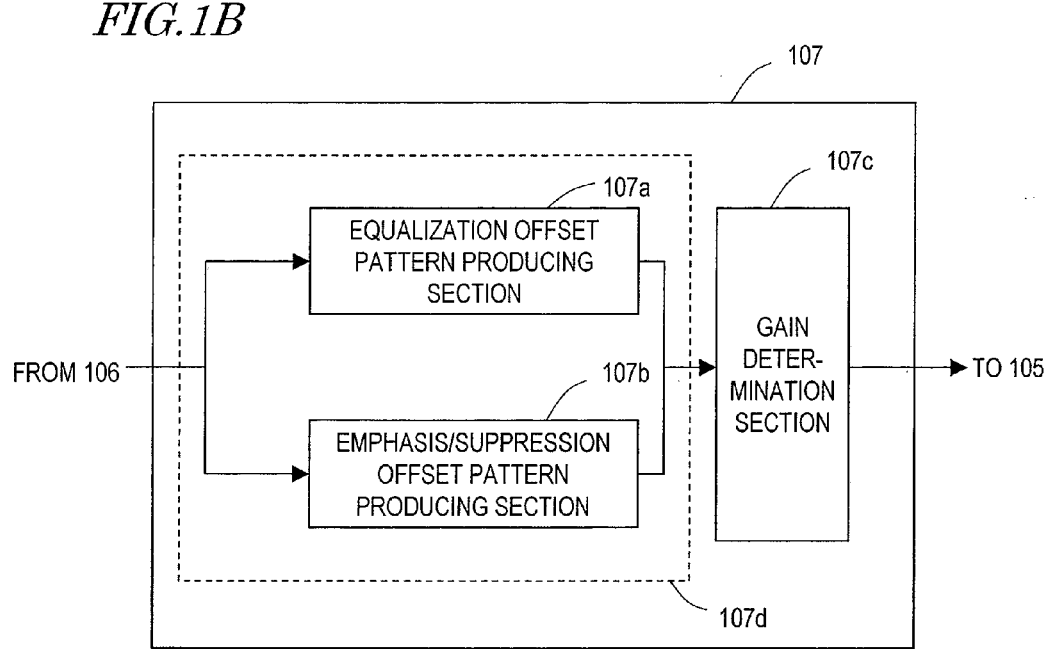
FIG. 1B is a block diagram of a gain control section.

In response to the operator operating the input section 111 or in accordance with the control by the control section 115 based on an instruction to the input section 111, the gain control section 107 determines the set gain with which the brightness of the tomographic image is adjusted so as to make the tomographic image frame easier to view, based on the brightness information of pixels of the tomographic image frame stored in the frame memory 106. FIG. 1B is a block diagram showing the function of the gain control section 107. As shown in FIG. 1B, the gain control section 107 includes an offset pattern producing section 107*d* and a gain determination section 107*c*, the offset pattern producing section 107*d* including an equalization offset pattern producing section 107*a*, and an emphasis/suppression offset pattern producing section 107*b*.

Figure 2:
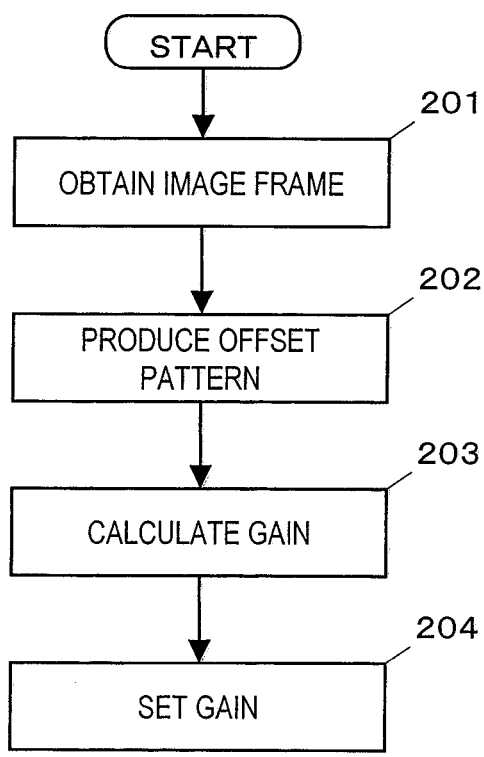
FIG. 2 is a flow chart showing an operation of the gain control section.

FIG. 2 is a flow chart showing an operation of the gain control section 107. In step 201, the offset pattern producing section 107*d* reads out the brightness information of pixels of the tomographic image frame stored in the frame memory 106. Then, in step 202, at least one offset pattern is produced, made up of brightness offset values for different pixels based on the brightness information of the different pixels of the tomographic image frame. The offset pattern is two-dimensional data, which is to be applied to the entire tomographic image frame. More preferably, the equalization offset pattern producing section 107*a* and the emphasis/suppression offset pattern producing section 107*b* produce an equalization offset pattern and an emphasis/suppression offset pattern, respectively. The equalization offset pattern has an effect of generally equalizing the brightness level across the tomographic image frame. The emphasis/suppression offset pattern has an effect of emphasizing the anatomical component of the tomographic image frame while suppressing the noise component thereof.

In step 203, the gain determination section 107*c* determines, from the offset patterns, at least one of the total gain, the depth-direction gain, the scan-direction gain and the frame gain, and outputs to the image constructing section 105 the set gain, which is produced based on the at least one gain determined. In step 204, the image constructing section 105 receives the set gain, and applies the received set gain to the tomographic image frame. Thus, the brightness of the tomographic image frame is adjusted. The total gain is composed of a single offset value used for the entire tomographic image frame. The depth-direction gain and the scan-direction gain are composed of offset values used in the depth direction and in the scan direction, respectively, of the tomographic image frame. The frame gain is composed of offset values used for different pixels of the tomographic image frame.

Based on the set gain determined as described above, the image constructing section 105 adjusts the brightness of the tomographic image frame, which is produced for each passage of a predetermined period of time, using the same gain until the set gain is updated. The set gain is updated when the operator gives an instruction to the input section 111.

Next, the operation of the gain control section 107 and the set gain produced by the gain control section 107 will be described in detail through the steps shown in FIG. 2.

1. Obtaining Tomographic Image Frame (Step 201)

As described above, based on an operator's instruction from the input section 111, the gain control section 107 reads out the brightness information of pixels of the tomographic image frame stored in the frame memory 106. The gain control section 107 may apply, to the brightness information of the read-out tomographic image frame, a spatial filter, etc., for reducing noise contained in the brightness information of the tomographic image frame or emphasizing lines and edges in the image, in a manner that suits subsequent processes.

2. Producing Offset Patterns (Step 202)

Figure 3:
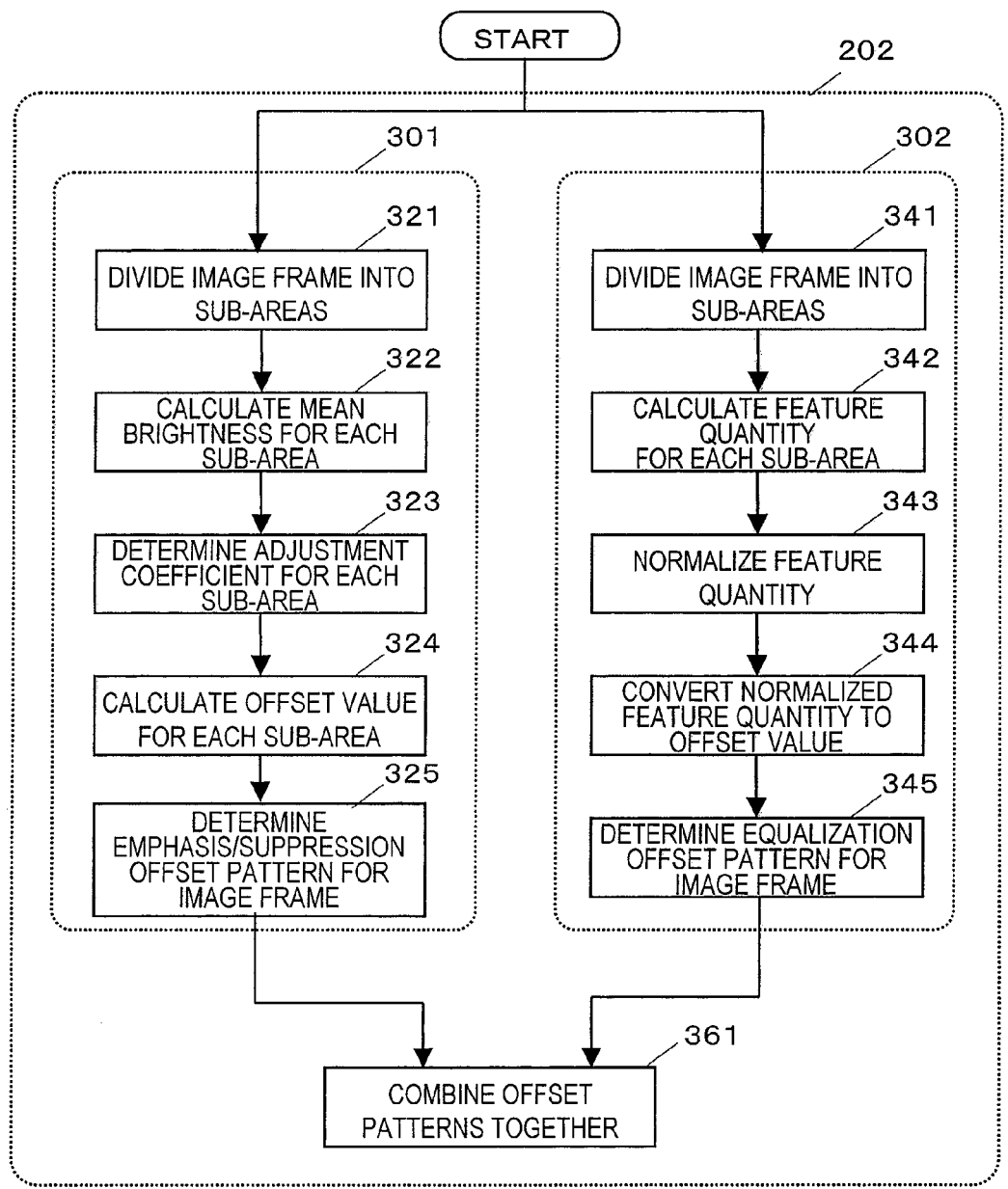
FIG. 3 is a flow chart showing an operation of an offset pattern producing section.

FIG. 3 is a flow chart showing the process of producing an offset pattern in step 202. The equalization offset pattern producing section 107a of the gain control section 107 produces an equalization offset pattern based on the brightness information of pixels of the tomographic image frame through the process of a group of steps 301, and the emphasis/suppression offset pattern producing section 107b produces an emphasis/suppression offset pattern based on the brightness information of pixels of the tomographic image frame through the process of a group of steps 302. These two steps may be performed simultaneously or successively, depending on the processing capacity of the gain control section. With successive processing, either offset pattern may be produced first.

First, the process of producing an equalization offset pattern (the group of steps 301) will be described.

Figure 4:
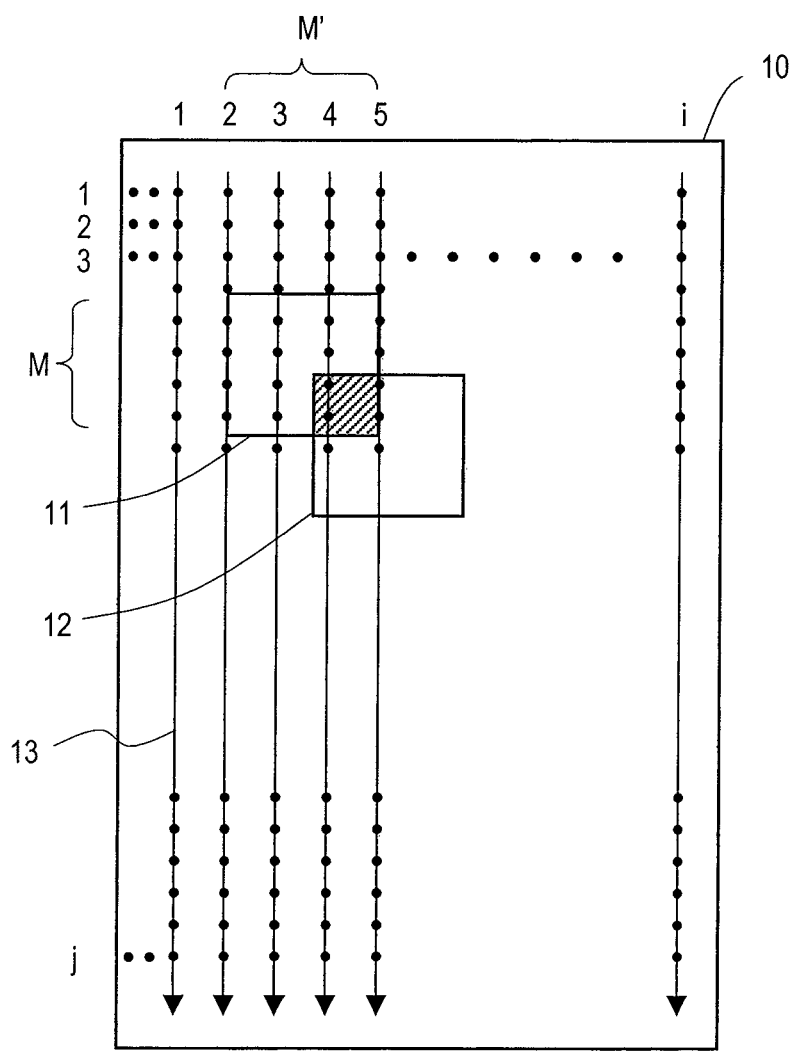
FIG. 4 shows sub-areas to be defined in a tomographic image frame.

As shown in FIG. 4, a tomographic image frame 10 is obtained by scanning an object with an ultrasonic beam having acoustic lines 13, and a plurality of measurement points (denoted by dots) are arranged at regular intervals along each acoustic line 13. Where the number of acoustic lines of the tomographic image frame 10 is i, and the number of measurement points along each acoustic line 13 is j, the tomographic image frame 10 is composed of i×j pixels. First, in step 321 of FIG. 3, a tomographic image frame obtained is divided into sub-areas 11, each including M×N pixels. M and N may each be set to an arbitrary value (M≤i, N≤j) in advance. Sub-areas may partially overlap with each other, as shown by sub-areas 11 and 12 in FIG. 4, for example.

Then, in step 322, the mean brightness for all pixels in each of the sub-areas 11 is calculated.

Figure 5:
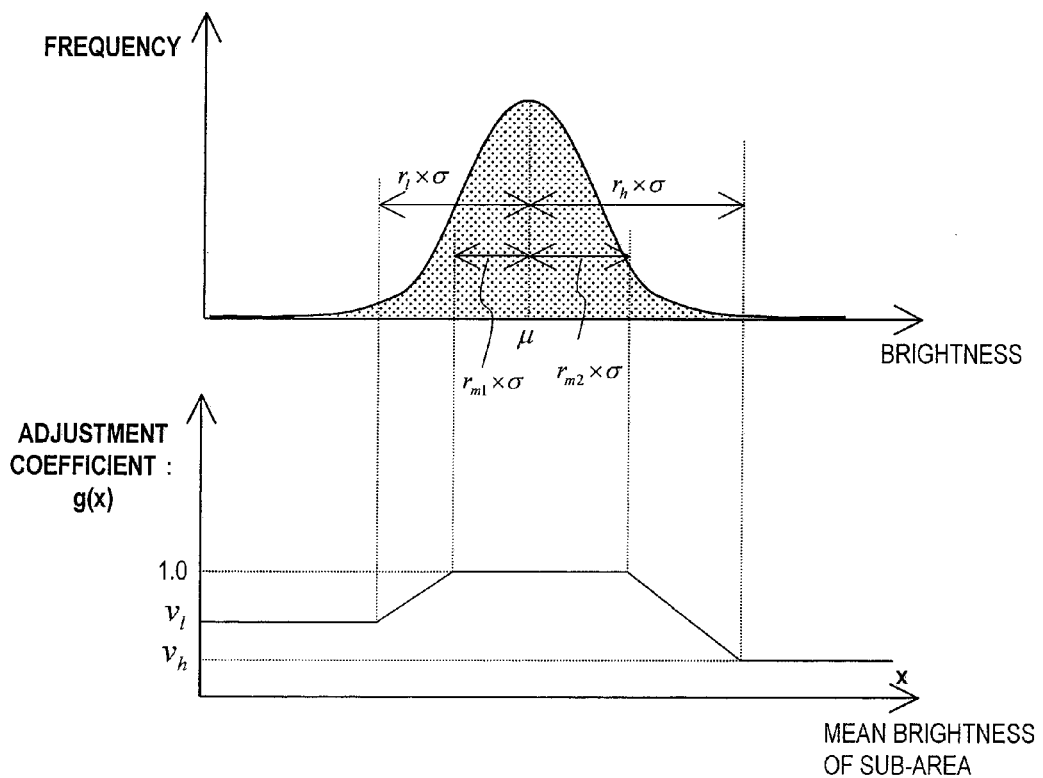
FIG. 5 shows a method for determining the adjustment coefficient based on the mean brightness of the sub-area.

Then, in step 323, the adjustment coefficient of each sub-area is calculated. The method for determining the adjustment coefficient is shown in FIG. 5. First, the mean brightness $\mu$ and the standard deviation $\sigma$ of brightness for all pixels of the tomographic image frame are obtained. Where a histogram of brightness for all pixels is as shown in the upper graph of FIG. 5, an adjustment coefficient $g(x)$ is determined in accordance with the brightness as shown in the lower graph of FIG. 5. Specifically, the adjustment coefficient is set to 1 if the brightness is $\mu - r_{m1} \times \tau$ or more and $\mu + r_{m2} \times \sigma$ or less, and the adjustment coefficient is set to $v_l$ or $v_h$ if the brightness is $\mu - r_l \times \sigma$ or less or $\mu + r_h \times \sigma$ or more, respectively. The adjustment coefficient is set to a value from $v_l$ to 1 in proportion to the brightness if the brightness is $\mu - r_l \times \sigma$ or more and $\mu - r_{m1} \times \sigma$ or less. Similarly, the adjustment coefficient is set to a value from 1 to $v_h$ in proportion to the brightness if the brightness is $\mu + r_{m2} \times \sigma$ or more and $\mu + r_h \times \sigma$ or less. The coefficients $r_l$, $r_{m1}$, $r_{m2}$, $r_h$, $v_l$ and $v_h$ may each be set to an arbitrary value in advance, and may be varied depending on the part of the subject to be imaged and/or the type of the probe used.

Then, in step 324, the optimal offset value is calculated for each sub-area as shown in Expression 1 below.

$$\text{Offset}[m,n] = (\mu - \mu_{m,n}) \times g(\mu_{m,n}) \qquad \text{Expression 1}$$

Offset[m,n]: Offset value of sub-area (m,n)
$\mu$: Mean brightness of image frame
$\mu_{m,n}$: Mean brightness of sub-area (m,n)
$g(x)$: Adjustment coefficient As can be seen from Expression 1 and FIG. 5, if the mean brightness $\mu_{m,n}$ of a sub-area is equal to the mean brightness $\mu$ for all pixels of the tomographic image frame, the offset [m,n] is zero. If the mean brightness $\mu_{m,n}$ of a sub-area is significantly apart from the mean brightness $\mu$ for all pixels of the tomographic image frame, i.e., if the brightness is significantly higher (brighter) or significantly lower (darker), the adjustment coefficient $g(x)$ is set to a small value of $v_l$ or $v_h$. Thus, the offset value shown in Expression 1 is small in sub-areas where the mean brightness $\mu_{m,n}$ is low or high. The application of such offset values to a tomographic image frame emphasizes gray level differences in portions of the average brightness, while reducing gray level differences in significantly dark portions and in significantly bright portions.

Figure 6:
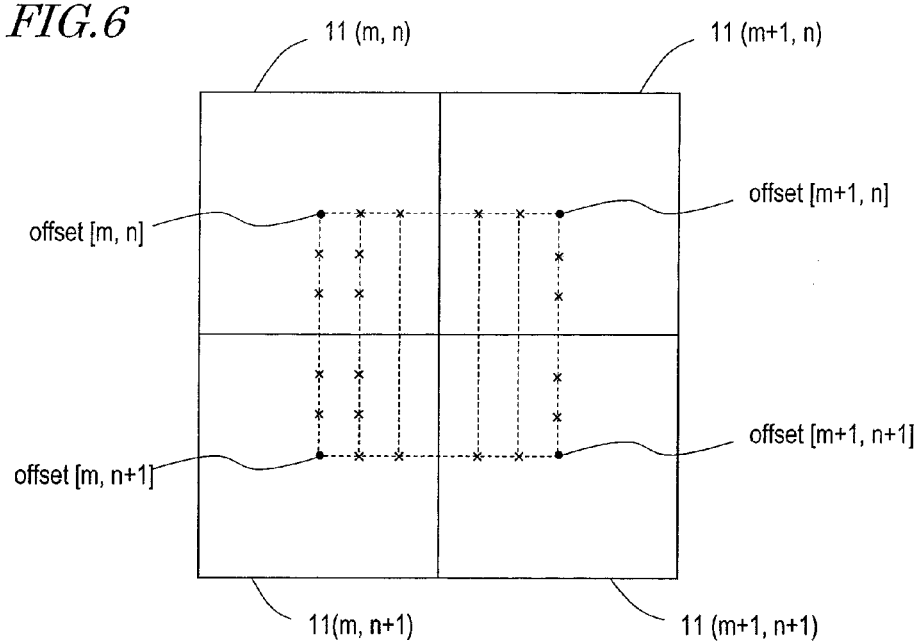
FIG. 6 shows a method for obtaining interpolated values at positions of different pixels based on values of sub-areas.

Then, in step 325, each offset value is plotted at the central point of the corresponding sub-area, and values of points between the central points of adjacent sub-areas are interpolated by linear interpolation, thereby obtaining offset values of all pixels of the image frame. As shown in FIG. 6, offset values at positions of pixels located along the straight line extending between the centers of the sub-areas 11(m,n) and 11(m+1,n) are obtained by linear interpolation, based on the offset [m,n] and the offset [m+1,n]. Similarly, offset values at positions of pixels located along the straight line extending between the centers of the sub-areas 11(m,n+1) and 11(m+1,n+1) are obtained by linear interpolation, based on the offset [m,n+1] and the offset [m+1,n+1]. Then, using the interpolated values, it is possible to obtain offset values at positions of pixels surrounded by the centers of the sub-areas 11(m,n), 11(m+1,n), 11(m+1,n) and 11(m+1,n+1). Thus, it is possible to obtain offset values of all pixels of the tomographic image frame. This set of offset values is referred to as an "equalization offset pattern". The offset value at the position (x,y) in the equalization offset pattern is represented as EqPat[x,y] (x=1 to i, y=1 to j).

Next, the process of producing an emphasis/suppression offset pattern (the group of steps 302) will be described. First, in step 341, the sub-areas 11 are defined, as in the process of producing an equalization offset pattern. Then, in step 342, the mean brightness Mean and the standard deviation StdDev of brightness are obtained for each sub-area 11, and the feature quantity Fv of the sub-area 11 is calculated as shown in Expression 2 below.

$$Fv = \text{Mean} \times \text{StdDev}^v \qquad \text{Expression 2}$$

Mean: Mean brightness
StdDev: Standard deviation of brightness
v: Exponent coefficient The exponent coefficient v may be set to an arbitrary value in advance. For example, the exponent coefficient v is a value in the range from 0.1 to 2.0. If the sub-area 11 includes a tissue boundary, the brightness therein will be high because a tissue boundary gives an increased reflection of ultrasonic wave, and the variance, i.e., the standard deviation, of the brightness will also be large. Accordingly, the feature quantity Fv will also be large. If the sub-area 11 includes a blood flow, the brightness therein will be low because a blood flow gives a weak reflection of ultrasonic wave, and the standard deviation of brightness will also be small. Accordingly, the feature quantity Fv will also be small. This trend is similarly seen also in cases where the sub-area 11 contains a large noise component. Thus, by evaluating the feature quantity of a sub-area 11 by using, as the feature quantity Fv, a function of the mean brightness and the standard deviation of brightness, it is possible to estimate whether there is noise or a tissue boundary in the sub-area 11. The exponent coefficient v is preferably set to a higher value if the tomographic image includes a tissue boundary that is desirably emphasized.

Then, in step 343, the feature quantity Fv is normalized as shown in Expression 3 below.

$$Norm(Fv_{m,n}) = \frac{Fv_{m,n} - \text{Mean}}{\text{StdDev}} \quad \text{Expression 3}$$

Figure 7:
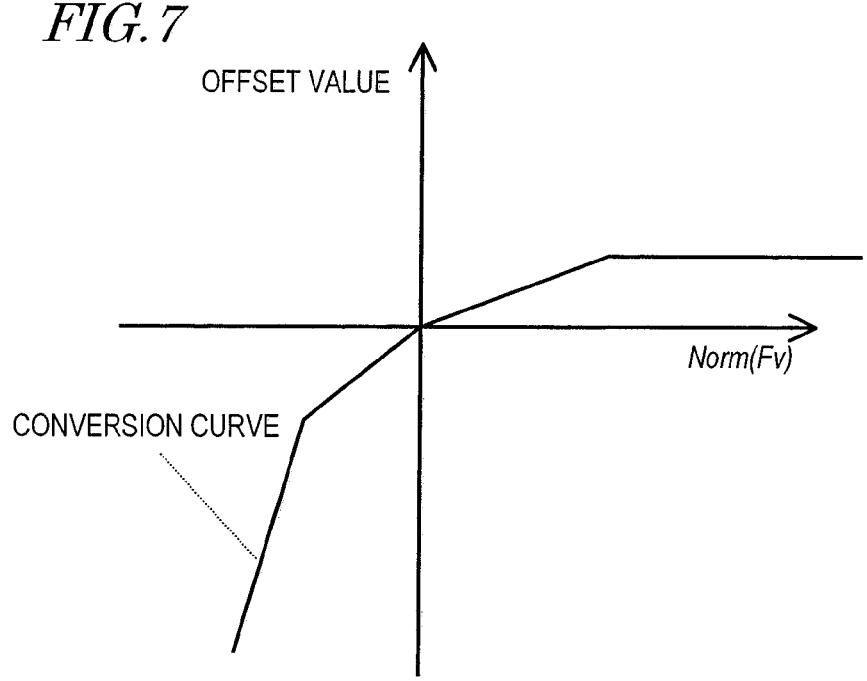
FIG. 7 shows a method for determining an offset value based on a normalized feature quantity.

$Fv_{m,n}$: Feature quantity of sub-area (m,n)
Mean: Mean for feature quantity collection
StdDev: Standard deviation for feature quantity collection The normalized feature quantity Norm (Fv) is converted to an offset value by, for example, using a conversion curve shown in FIG. 7. The conversion curve may be set to an arbitrary shape in advance, and may be varied depending on the part of the subject to be imaged and/or the type of the probe used. In the conversion curve shown in FIG. 7, the offset value is smaller and varies more in the region where the normalized feature quantity Norm (Fv) is smaller. The normalized feature quantity Norm (Fv) of a sub-area 11 being small means that the sub-area 11 has a weak reflection of ultrasonic wave or contains a large noise component. Therefore, it is possible to remove the influence of noise by setting a small offset value to be applied to such a sub-area 11, and thus minimizing the brightness of the sub-area 11 in the tomographic image. In contrast, the normalized feature quantity Norm (Fv) of a sub-area 11 being large means that the sub-area 11 has a strong reflection of ultrasonic wave, and it is not necessary to use a large offset value to emphasize the brightness in such a sub-area 11.

Then, in step 345, each offset value is plotted at the central point of the corresponding sub-area, and values of points between the central points of adjacent sub-areas are interpolated by linear interpolation, thereby obtaining offset values of all pixels of the image frame. These values can be obtained by such a method as described above with reference to FIG. 6. Thus, it is possible to obtain offset values of all pixels of the tomographic image frame. This set of offset values is referred to as an "emphasis/suppression offset pattern". The offset value at the position (x,y) in the emphasis/suppression offset pattern is represented as EmPat[x,y] (x=1 to i, y=1 to j).

Then, in step 361, the equalization offset pattern and the emphasis/suppression offset pattern are combined together as shown in Expression 4 below. The weighting coefficients C1 and C2 may each be set to an arbitrary value in advance.

$$\text{Offset}(x,y) = C1 \times \text{EqPat}(x,y) + C2 \times \text{EmPat}(x,y) \quad \text{Expression 4}$$

Offset(x,y): Offset value at position (x,y) in optimized offset pattern
C1, C2: Weighting coefficients 3. Calculating Gain (Step 203)

Figure 8:
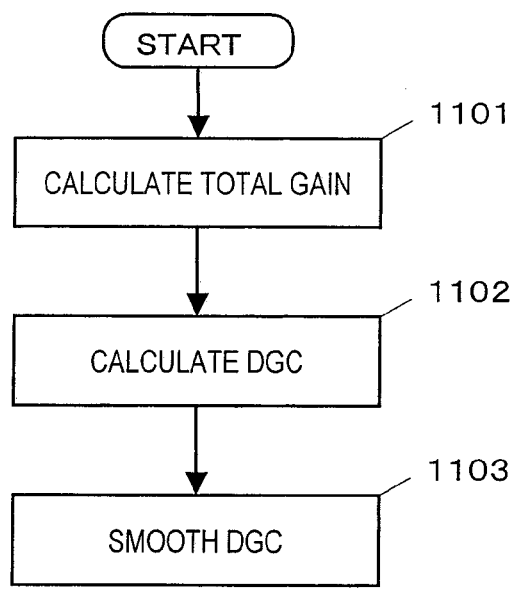
FIG. 8 is a flow chart showing a process of calculating a gain from an offset pattern.

FIG. 8 is a flow chart showing a process of calculating a gain from an offset pattern. In step 1101, the gain determination section 107*c* calculates the total gain BaseGain from the offset pattern as shown in Expression 5 below. The total gain BaseGain is a single offset value to be applied to all pixels of the tomographic image frame.

$$\text{BaseGain} = \frac{1}{W \times H} \sum_{x=0}^{W-1} \sum_{y=0}^{H-1} \text{offset}(x, y) \quad \text{Expression 5}$$

Offset(x,y): Offset value at position (x,y) in offset pattern
W: Width of offset pattern
H: Height of offset pattern Then, in step 1102, the depth-direction gain DgcValue[y] is calculated as shown in Expression 6 below. The depth-direction gain DgcValue[y] is a series of offset values arranged in the depth direction, and is commonly applied to all pixels along the same acoustic line. Then, in step 1103, the depth-direction gain DgcValue[y] is low-pass-filtered to thereby smooth the depth-direction gain DgcValue[y]. While a low-pass filter is used for the smoothing of the depth-direction gain DgcValue[y] in the present embodiment, a non-linear filter, or the like, such as a median filter may be used in other embodiments.

$$\text{DgcValue}[y] = \frac{1}{W} \sum_{x=0}^{W-1} \text{offset}(x, y) - \text{BaseGain} \quad \text{Expression 6}$$

Offset(x,y): Offset value at position (x,y) in offset pattern
W: Width of offset pattern Through such a process, the depth-direction gain DgcValue[y] obtained in the gain control section 107 is outputted to the image constructing section 105 as the set gain. The image constructing section 105 adjusts the brightness of the tomographic image frame by using the received depth-direction gain DgcValue[y], and outputs the adjusted tomographic image frame to the display section 108.

While the total gain and the depth-direction gain are obtained in the present embodiment, the scan-direction gain may be obtained by a similar process in other embodiments. The frame gain including offset values used for different pixels of the tomographic image frame may be obtained in other embodiments. The scan-direction gain TgcValue[x] and the frame gain FrameGain(x,y) may be calculated, for example, as shown in Expressions 7 and 8 below.

$$\text{TgcValue}[x] = \frac{1}{H} \sum_{y=0}^{H-1} \text{offset}(x, y) - \text{BaseGain} \quad \text{Expression 7}$$

Offset(x,y): Offset value at position (x,y) in offset pattern
H: Height of offset pattern $$\text{FrameGain}(x,y) = \text{offset}(x,y) - \text{BaseGain} \quad \text{Expression 8}$$

With the ultrasonic diagnostic apparatus of the present embodiment, the gain control section 107 two-dimensionally performs a statistical operation on the brightness data of the tomographic image obtained by transmitting and then receiving an ultrasonic wave, thereby automatically producing a gain with which the brightness can be adjusted so as to obtain an image that is easier to view. Therefore, it is possible to obtain a tomographic image with such a brightness that the image is easy to view without the operator performing a complicated operation.

Since a statistical operation is two-dimensionally performed on the brightness data of the tomographic image, it is possible to obtain a tomographic image in which an anatomical tissue component is shown with even brightness even if an anatomical tissue component is contained in the tomographic image, unlike with a gain adjustment by DGC or LGC.

The ultrasonic diagnostic apparatus of the present embodiment independently performs the production of an offset pattern for a brightness adjustment for achieving a tomographic image with even brightness that is easy to view, and the production of an offset pattern for removing noise contained in a tomographic image and better defining the shape of each tissue. Therefore, it is possible to perform an optimal brightness adjustment with respect to these two different objectives.

Second Embodiment

Figure 9:
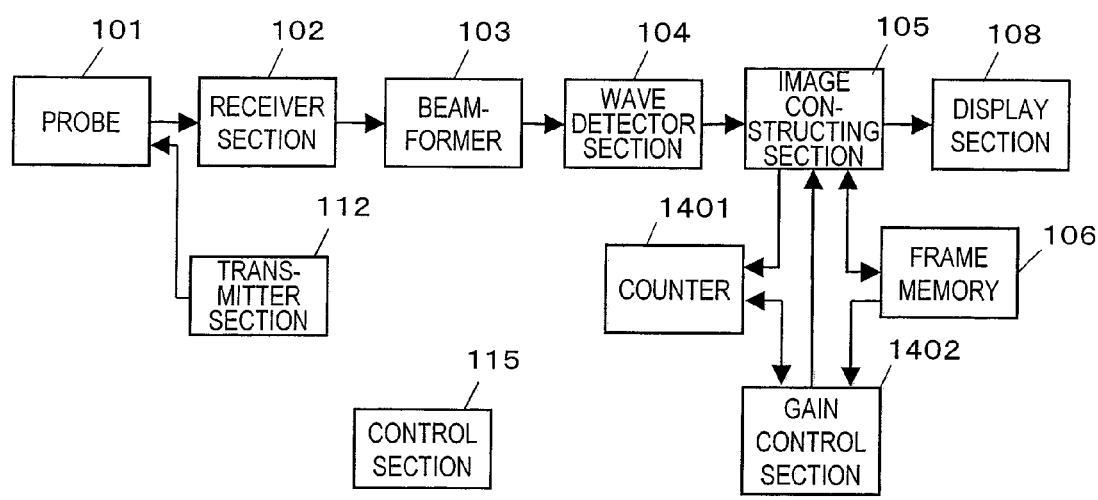
FIG. 9 is a block diagram showing an ultrasonic diagnostic apparatus according to a second embodiment of the present invention.

FIG. 9 is a block diagram showing an ultrasonic diagnostic apparatus according to a second embodiment of the present invention. The present embodiment differs from the first embodiment in that the ultrasonic diagnostic apparatus of the present embodiment includes a counter 1401, wherein the counter 1401 counts the number of image frames produced, and a gain control section 1402 produces a gain based on the count of the counter 1401. Otherwise, the ultrasonic diagnostic apparatus of the present embodiment includes the same elements as those of the first embodiment.

The image constructing section 105 outputs the produced image frame to the frame memory 106, and increments the counter value of the counter 1401 each time an image frame is produced.

The gain control section 1402 refers to the counter value of the counter 1401, and when the counter value reaches a predetermined number N, the gain control section 1402 reads out the tomographic image frame from the frame memory 106 and calculates the set gain, as described above in the first embodiment. The gain control section 1402 also resets the counter 1401. The gain produced by the gain control section 1402 is outputted to the image constructing section 105. The image constructing section 105 adjusts the brightness of the tomographic image frame using the received gain, and outputs the adjusted tomographic image frame to the display section 108. The equalization offset pattern and the emphasis/suppression offset pattern may be produced to determine the set gain, as in the first embodiment, or the frequency with which the equalization offset pattern and the emphasis/suppression offset pattern are produced may be varied based on the counter value.

If the number N is set to be large, the frequency with which the gain control section 1402 produces a gain is decreased, thereby reducing the load on the gain control section 1402, but deteriorating the precision of tomographic image brightness adjustment. If the number N is set to be small, the frequency of gain production is increased, thereby improving the precision of tomographic image brightness adjustment, but increasing the load on the gain control section 1402. Therefore, the value of N is preferably determined based on the capacity of the gain control section 1402 or of the processor for executing the software implementing the function of the gain control section 1402, and the level of precision required of the tomographic image. The value of N may be variable based on the rate of the tomographic image frame, instead of being a fixed value.

While both of the equalization offset pattern and the emphasis/suppression offset pattern are produced in the first and second embodiments, a set of offset values may be produced by producing only one of these offset patterns in view of the characteristics of the subject.

While the ultrasonic diagnostic apparatus only has a function of displaying a tomographic image in the first and second embodiments, the ultrasonic diagnostic apparatus may also have a function of measuring the distribution of the blood flow, the characteristic of the blood flow, the elastic characteristic of the subject's tissue, etc.

The present invention is suitable for use in an ultrasonic diagnostic apparatus for displaying a tomographic image of a subject, and is also suitable for use in an ultrasonic diagnostic apparatus for measuring the distribution of the blood flow, the characteristic of the blood flow, the elastic characteristic of the subject's tissue, etc., in addition to displaying a tomographic image.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

This application is based on Japanese Patent Applications No. 2008-239228 filed on Sep. 18, 2008, the entire contents of which are hereby incorporated by reference.

What is claimed is:

1. An ultrasonic diagnostic apparatus comprising:
a transmitter circuit configured to drive a probe so that a subject is scanned with an ultrasonic beam over a predetermined period of time;
a receiver circuit configured to receive, using the probe, an echo resulting from the ultrasonic beam being reflected by the subject, and configured to produce a receive signal for each passage of the predetermined period of time;
an image constructing microprocessor configured to produce a tomographic image frame composed of brightness information based on an intensity of the receive signal for each passage of the predetermined period of time, and configured to adjust brightness of the produced tomographic image frame with a set gain, the tomographic image being composed of a plurality of pixels arranged in two dimensions;
a gain control microprocessor configured to produce the set gain; and
a display for displaying the tomographic image frame whose brightness has been adjusted,
wherein the gain control microprocessor includes:
an offset pattern producing microprocessor configured to produce at least one offset pattern based on brightness information for each pixel of the tomographic image frame, the offset pattern including brightness offset values for the each pixel; and
a gain determination microprocessor configured to determine the set gain based on at least one gain, selected from among a total gain, a depth-direction gain, a scan-direction gain and a frame gain, based on the offset pattern, wherein the total gain is composed of a single offset value used for the entire tomographic image frame, the depth-direction gain includes offset values used in a depth direction of the tomographic image frame, the scan-direction gain includes offset values used in a scan direction of the tomographic image frame, and the frame gain includes offset values used for different pixels of the tomographic image frame,
wherein the offset pattern producing microprocessor includes an equalization offset pattern producing microprocessor configured to produce an equalization offset pattern in two dimensions for equalizing a brightness level of the tomographic image frame, and
wherein the offset pattern producing microprocessor includes an emphasis/suppression offset pattern producing microprocessor configured to produce an emphasis/suppression offset pattern for emphasizing a tissue while suppressing a noise component in the tomographic image frame, where the emphasis/suppression offset pattern is based on a feature quantity of each of a plurality of sub-areas of the tomographic image frame, the feature quantity of each of the sub-areas being a function of a mean brightness parameter and a standard deviation of the brightness parameter in the each of the sub-areas according to the formula:

$$Fv = \text{Mean} \times \text{stdDev}^v,$$

where
Fv: Feature quantity
Mean: Mean brightness
StdDev: Standard deviation of brightness
v: Predetermined exponent coefficient.

2. The ultrasonic diagnostic apparatus according to claim 1, wherein the gain control microprocessor produces the set gain based on an instruction from an operator.

3. The ultrasonic diagnostic apparatus according to claim 1, further comprising:
a counter microprocessor that counts the number of the tomographic image frames produced,
wherein the gain control microprocessor produces the set gain based on the number of the tomographic image frames produced.

4. The ultrasonic diagnostic apparatus according to claim 3, wherein the gain control microprocessor determines a frequency with which the set gain is produced based on a frame rate at which the tomographic image frame is produced.

5. The ultrasonic diagnostic apparatus according to claim 3, wherein the gain control microprocessor produces a plurality of offset patterns, and sets a frequency with which the offset patterns are produced based on the number of tomographic image frames produced.

6. The ultrasonic diagnostic apparatus according to claim 1, wherein the equalization offset pattern producing microprocessor:
divides the tomographic image frame into a plurality of sub-areas;
calculates a mean brightness of each sub-area;
calculates a brightness difference between the mean brightness of the subarea and a reference brightness;
determines an adjustment value by which the brightness difference is multiplied;
determines a product obtained by multiplying the brightness difference by the adjustment value to be an offset value for the sub-area; and
calculates the equalization offset pattern including offset values for all pixels of the tomographic image frame based on the offset values for the sub-areas.

7. The ultrasonic diagnostic apparatus according to claim 6, wherein the reference brightness is a mean brightness for the entire tomographic image frame.

8. The ultrasonic diagnostic apparatus according to claim 6, wherein the adjustment value is determined based on a brightness value histogram for the sub-area and a brightness value histogram for the entire image frame.

9. The ultrasonic diagnostic apparatus according to claim 1, wherein the emphasis/suppression offset pattern producing microprocessor:
divides the tomographic image frame into sub-areas;
calculates the feature quantity of each sub-area;
normalizes the feature quantity;
converts the normalized feature quantity to an offset value; and
calculates the emphasis/suppression offset pattern including offset values for all pixels of the tomographic image frame based on the offset values for the subareas.

10. The ultrasonic diagnostic apparatus according to claim 9, wherein normalized feature quantity is converted to an offset value using a conversion curve.

11. The ultrasonic diagnostic apparatus according to claim 1, wherein the single offset value of the total gain is a mean value among all pixels of the offset pattern.

12. The ultrasonic diagnostic apparatus according to claim 1, wherein the gain determination microprocessor calculates a mean value among offset values for pixels of the same depth in the offset pattern, and calculates the depth-direction gain by smoothing the mean value in the depth direction.

13. The ultrasonic diagnostic apparatus according to claim 1, wherein the gain determination microprocessor calculates a mean value among offset values for pixels along the same scan line in the offset pattern, and calculates the scan-direction gain by smoothing the mean value in the scan direction.

* * * * *